United States Patent
Hoshino et al.

(10) Patent No.: US 8,349,254 B2
(45) Date of Patent: Jan. 8, 2013

(54) CIRCUIT FOR COLLECTING BLOOD COMPONENT AND APPARATUS FOR COLLECTING BLOOD COMPONENT

(75) Inventors: Yoshiteru Hoshino, Fujinomiya (JP); Yoshihiro Yokoo, Fujinomiya (JP); Yuusuke Yamazaki, Shibuya-ku (JP)

(73) Assignee: Terumo Kabushiki Kaisha, Shibuya-Ku, Tokyo (JP)

(*) Notice: Subject to any disclaimer, the term of this patent is extended or adjusted under 35 U.S.C. 154(b) by 732 days.

(21) Appl. No.: 11/988,105

(22) PCT Filed: Jul. 4, 2006

(86) PCT No.: PCT/JP2006/313328
§ 371 (c)(1),
(2), (4) Date: Dec. 31, 2007

(87) PCT Pub. No.: WO2007/007596
PCT Pub. Date: Jan. 18, 2007

(65) Prior Publication Data
US 2009/0129976 A1 May 21, 2009

(30) Foreign Application Priority Data
Jul. 8, 2005 (JP) .................. 2005-200623

(51) Int. Cl.
- G01N 21/75 (2006.01)
- G01N 33/48 (2006.01)
- G01N 33/86 (2006.01)
- A61M 37/00 (2006.01)
- A61M 1/00 (2006.01)
- A61M 1/36 (2006.01)
- A61M 1/38 (2006.01)

(52) U.S. Cl. ........ 422/44; 604/4.01; 604/5.01; 604/5.02; 604/5.03; 604/5.04; 604/6.01; 604/6.07; 604/6.1; 604/6.11; 604/6.13; 604/6.14; 604/6.15

(58) Field of Classification Search .......... 422/44; 604/5.01, 6.01, 6.05, 6.07, 6.15
See application file for complete search history.

(56) References Cited

U.S. PATENT DOCUMENTS
4,902,282 A * 2/1990 Bellotti et al. ............. 604/258
(Continued)

FOREIGN PATENT DOCUMENTS
CN 2623169 Y 7/2004
(Continued)

OTHER PUBLICATIONS
PCT/ISA/210 and PCT/ISA/237 for PCT/JP2006/313328 dated Oct. 10, 2006.
(Continued)

Primary Examiner — Leslie Deak
Assistant Examiner — Adam Marcetich
(74) Attorney, Agent, or Firm — Buchanan Ingersoll & Rooney PC

(57) ABSTRACT

A circuit for collecting a blood component includes a blood collection device provided with a blood collection needle through which blood is collected from a blood donor, a blood separator in which the blood collected by the above blood collection device is separated, a blood component collection bag in which a predetermined blood component separated by the above blood separator is collected, a blood line in which the blood collection needle is connected to an inlet of the blood separator, a line for removing an initial blood flow, which branches from a first branching portion formed in the blood line, and in which an initial flow of blood collected from the blood donor is removed, and an anticoagulant-injection line that branches from a second branching portion, formed in the line for removing the initial blood flow, and into which an anticoagulant is injected.

16 Claims, 2 Drawing Sheets

U.S. PATENT DOCUMENTS

| | | | |
|---|---|---|---|
| 5,250,041 A * | 10/1993 | Folden et al. | 604/284 |
| 5,348,533 A * | 9/1994 | Papillon et al. | 604/6.07 |
| 5,387,187 A | 2/1995 | Fell et al. | |
| 5,494,592 A * | 2/1996 | Latham et al. | 210/805 |
| 5,607,579 A | 3/1997 | Latham, Jr. et al. | |
| 5,954,971 A * | 9/1999 | Pages et al. | 210/739 |
| 6,026,684 A * | 2/2000 | Calder | 73/379.02 |
| 6,328,726 B1 | 12/2001 | Ishida et al. | |
| 6,592,613 B1 * | 7/2003 | Ishida et al. | 604/408 |
| 6,692,479 B2 * | 2/2004 | Kraus et al. | 604/410 |
| 6,849,039 B2 | 2/2005 | Min et al. | |
| 6,899,691 B2 | 5/2005 | Bainbridge et al. | |
| 7,087,047 B2 * | 8/2006 | Kraus et al. | 604/408 |
| 7,566,315 B2 * | 7/2009 | Hirabuki | 604/6.01 |
| 2001/0048892 A1 * | 12/2001 | Bainbridge et al. | 422/44 |
| 2002/0131891 A1 * | 9/2002 | Smith et al. | 422/44 |
| 2003/0208151 A1 * | 11/2003 | Kraus et al. | 604/4.01 |
| 2004/0186408 A1 * | 9/2004 | Behague et al. | 604/4.01 |

FOREIGN PATENT DOCUMENTS

| | | |
|---|---|---|
| CN | 2703527 Y | 6/2005 |
| JP | 5-38363 A | 2/1993 |
| JP | 8-504334 | 5/1996 |
| JP | 8-509403 A | 10/1996 |
| JP | 11-197236 A | 12/2001 |
| JP | 2005-110748 | 4/2005 |

OTHER PUBLICATIONS

Office Action issued Nov. 20, 2009 by the Patent Office of the People's Republic of China in Chinese Patent Application No. 2006800296752 and partial English language translation.

Front page of Grant Announcement No. CN101242864B, one page, Chinese Patent Office, Sep. 22, 2010 (with English translation).

* cited by examiner

CIRCUIT FOR COLLECTING BLOOD COMPONENT AND APPARATUS FOR COLLECTING BLOOD COMPONENT

TECHNICAL FIELD

The present invention relates to a circuit for collecting a blood component and an apparatus for collecting a blood component.

BACKGROUND ART

Component-basis blood collection is a procedure in which blood (whole blood) collected from a donor (blood donor) is separated into blood components by centrifugal separation or membrane separation, a necessary blood component is collected, and the residual blood components are returned to the donor. In the case of component-basis blood collection performed by a centrifugal separation system, particularly a centrifugal bowl system, in order to decrease infestation to the donor, a system in which a single blood collection needle is used, wherein a blood collection step and a blood returning step are repeated alternately, is adopted (refer to, for example, Japanese Laid-Open Patent Publication No. 8-509403 (PCT)).

In normal component-basis blood collection, alcoholic disinfection or the like is carried out. However, even after such a treatment, bacteria present on the skin or subcutaneous bacteria may become mixed in the blood component collection bag together with the blood component.

Depending on the kind of bacteria, the bacteria having thus become mixed may grow even during cold storage of the blood component collection bag, in which the blood component is contained. Therefore, when the blood component is served via transfusion without noticing the bacterial growth, a crisis, such as infectious disease or sepsis in the patient having received the transfusion, may occur.

In red blood cell conservation solutions (S.A.G.M. solutions, OPTISOL solutions, M.A.P. solutions, etc.) in use at present, the pH thereof is set comparatively near to neutral, unlike conventional blood conservation solutions (anticoagulants such as ACD-A solutions or CPD solutions). For this and other reasons, there is a high tendency toward bacterial growth during cold storage.

Such bacteria are often present not only on the surface of the skin but also subcutaneously. Therefore, penetration of such bacteria into the collected blood is difficult to obviate simply by conducting careful disinfection of the skin portion that is punctured by the blood collection needle.

Empirically, it is known that bacteria penetrates (together with debris of the skin, in most cases) mainly into the initial flow of the blood that is collected (the initial blood flow).

However, an apparatus for collecting a blood component is not known, in which the initial blood flow can be removed.

In view of this, in order to remove the initial blood flow, it may be contemplated to provide a line for removing the initial blood flow, which is branched from a branching portion formed in a blood line connected between the blood collection needle and the inlet of the blood separator, and by which the initial blood flow is removed.

In the aforementioned configuration, however, after the removal of the initial blood flow, blood that does not contain any anticoagulant may stagnate at the branching portion, at which the line for removing the initial blood flow branches from the blood line, and such stagnating blood may coagulate. If blood coagulates at the branching portion, such coagulated blood may flow (circulate) in the circuit and become mixed into the blood component in the blood component collection bag during blood collection, or such coagulated blood may be returned to the donor when the residual blood components are returned to the donor. Further, such coagulated blood may plug up the flow passage.

DISCLOSURE OF THE INVENTION

It is an object of the present invention to provide a circuit for collecting a blood component, as well as an apparatus for collecting a blood component, by which it is possible to prevent bacterial pollution of a collected blood component (blood), thereby enhancing safety, and preventing coagulation of blood at a first branching portion (a branching portion of a line through which an initial blood flow in the blood line is removed).

In order to attain the above object, the present invention provides a circuit for collecting a blood component, including:

a blood collection means provided with a blood collection needle for collecting blood from a blood donor;

a blood separator for separating the blood collected by the blood collection means;

a blood component collection bag for collecting a predetermined blood component separated by the blood separator;

a blood line connecting the blood collection needle and the inlet of the blood separator;

an initial flow removing line branched from a first branching portion formed in the blood line for removing the initial flow of the blood collected from the blood donor; and an anticoagulant-injection line branched from a second branching portion formed in the initial flow removing line for injecting an anticoagulant.

This makes it possible to prevent bacterial pollution of the collected blood component (blood), thereby enhancing safety, and preventing coagulation of the blood at the first branching portion (the branching portion of the line through which an initial blood flow in the blood line is removed).

In addition, in the circuit for collecting the blood component according to the present invention, preferably, the internal volume of a portion, between the first branching portion and the second branching portion, of the initial flow removing line is 0.05 to 1 mL.

This ensures that blood that does not contain any anticoagulant and which stagnates can be securely prevented from coming into proximity with the blood line, while also preventing the circuit for collecting the blood component from becoming large in size.

In addition, in order to attain the above object, the present invention provides:

an apparatus for collecting a blood component, including a circuit for collecting a blood component according to claim 1 or 2; and a supply means for adding the anticoagulant to the blood collected by the blood collection means, wherein blood collected from the blood donor is separated to thereby collect the predetermined blood component.

This makes it possible to prevent bacterial pollution of the collected blood component (blood), thereby enhancing safety, and preventing coagulation of the blood at the first branching portion (the branching portion of the line through which an initial blood flow in the blood line is removed).

In addition, in the apparatus for collecting a blood component according to the present invention, preferably, the supply means supplies the anticoagulant to the blood line through the anticoagulant-injection line, the second branching portion, a part of the initial flow removing line, and the first branching portion, after a predetermined amount of the initial blood flow is removed through the initial flow removing line.

This makes it possible to prevent blood that does not contain any anticoagulant from stagnating within the line for removing the initial blood flow and resulting in coagulation of the blood.

In addition, in the apparatus for collecting a blood component according to the present invention, preferably, the supply means comprises a liquid feed pump disposed within the anticoagulant-injection line.

This makes it possible to prevent blood that does not contain any anticoagulant from stagnating within the line for removing the initial blood flow and resulting in coagulation of the blood.

In addition, in the apparatus for collecting a blood component according to the present invention, preferably, the apparatus for collecting a blood component performs at least one cycle of a blood component collection process, including a blood component collection step by which the collected blood is separated and a predetermined blood component is collected therefrom, and a blood component returning step in which residual blood components are returned.

This ensures that the initial flow of the collected blood (initial blood flow), which has a high probability of bacterial infection, can easily be removed at the time of blood collection, and thus penetration of bacteria into a collected platelet concentrate, a platelet product, or into blood plasma can be restrained, thereby enhancing safety.

In addition, in the apparatus for collecting a blood component according to the present invention, preferably, the apparatus for collecting a blood component performs at least one cycle of a platelet collection process including a plasma collection step in which the collected blood is separated and plasma is collected, a plasma circulation step in which plasma collected by the plasma collection step is circulated in a blood separator, a platelet collection step in which plasma collected by the plasma collection step is accelerated and supplied into the blood separator, whereby platelets are collected, and a blood component returning step in which residual blood components are returned.

This ensures that the initial flow of the collected blood (initial blood flow), which has a high probability of bacterial infection, can easily be removed at the time of blood collection, and thus penetration of bacteria into a collected platelet concentrate, a platelet product, or into plasma can be restrained, thereby enhancing safety.

BEST MODE FOR CARRYING OUT THE INVENTION

A circuit for collecting a blood component, together with an apparatus for collecting a blood component, according to the present invention shall be described in detail below, based on a preferred embodiment as shown in the accompanying drawings.

Figure 1:
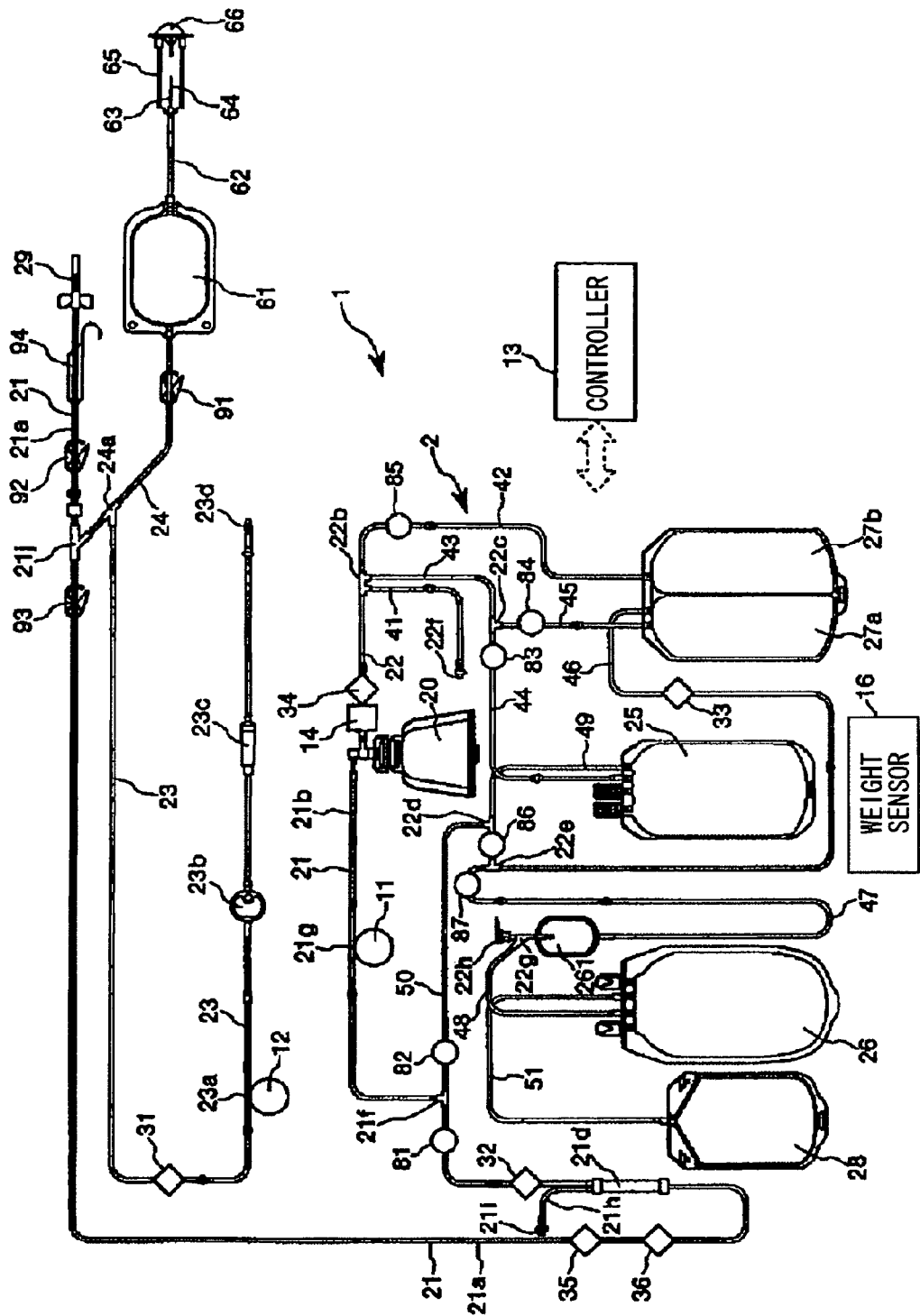
FIG. 1 is a plan view showing an embodiment of an apparatus for collecting a blood component according to the present invention.
Figure 2:
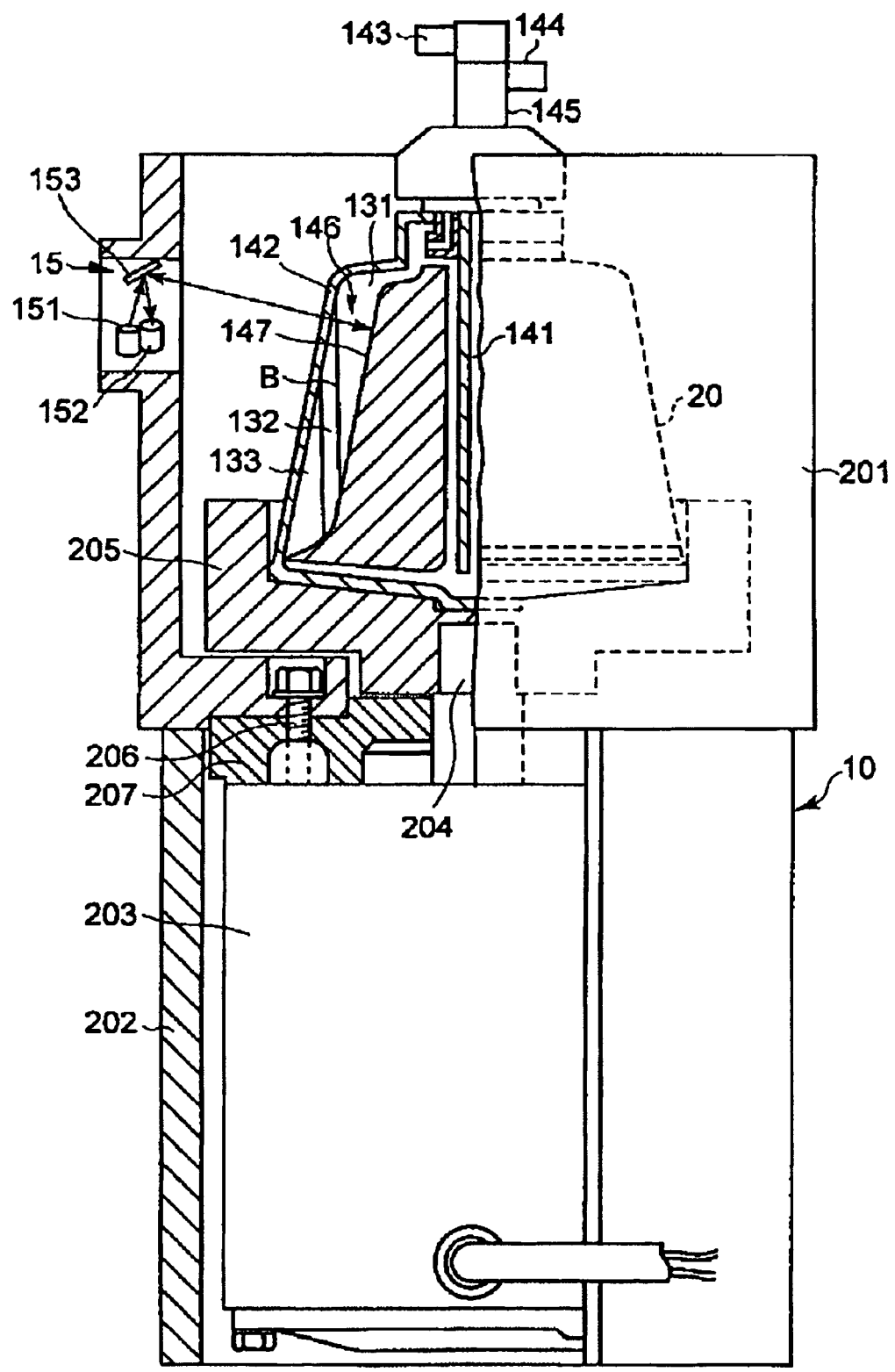
FIG. 2 is a partially broken sectional view, showing a condition in which a centrifugal separator is mounted on a centrifugal separator driving device, which is possessed by the apparatus for collecting a blood component shown in FIG. 1.

FIG. 1 is a plan view showing an embodiment of the apparatus for collecting a blood component according to the present invention, and FIG. 2 is a partially broken sectional view showing a condition in which a centrifugal separator is mounted on a centrifugal separator driving device, which is possessed by the apparatus for collecting a blood component shown in FIG. 1.

As shown in FIG. 1, the apparatus for collecting a blood component 1 is an apparatus for separating blood into a plurality of blood components and collecting the blood component(s) thus separated. In this embodiment, platelets (a platelet containing plasma) (blood component) and plasma (blood component) are collected. The apparatus for collecting a blood component 1 has a circuit for collecting the blood component (collection circuit) 2 including a rotor 142 provided therein with a blood reserving space 146, a centrifugal separator (blood separator) 20, which has an inlet 143 and a discharge port (outlet) 144 both communicating with the blood reserving space 146, by which the blood introduced through the inlet 143 by rotation of the rotor 142 is centrifugally separated in the blood reserving space 146, a first line (blood line) 21 connected between a blood collection needle 29 and the inlet 143 of the centrifugal separator 20, a second line 22 connected to the discharge port 144 of the centrifugal separator 20, a fourth line (initial flow removing line) (initial flow collection line) 24 connected to the first line 21, a third line (anticoagulant-injection line) 23 connected to the fourth line 24, a plasma collection bag (blood component collection bag) 25 connected to the first line 21 through tubes 49 and 50, and which is connected to the second line 22 through tubes 43 and 44, an air bag 27b connected to the second line 22 through a tube 42, an intermediate bag (temporary reserving bag) 27a connected to the second line 22 through tubes 43 and 45, a platelet collection bag (blood component collection bag) 26 connected to the intermediate bag 27a through tubes 46, 47 and 48, a bag 28 connected to the platelet collection bag 26 through a tube 51, and an initial flow collection bag 61 connected to the fourth line 24.

Furthermore, the apparatus for collecting a blood component 1 has a centrifugal separator driving device 10 for rotating the rotor 142 of the centrifugal separator 20, a first liquid feed pump 11 for the first line 21, a second liquid feed pump 12 for the third line 23, plural (in the present embodiment, seven, namely, first to seventh) passage opening/closing means 81, 82, 83, 84, 85, 86 and 87, which open and close intermediate portions of the passage in the circuit for collecting a blood component 2, a controller (control means) 13 for controlling the centrifugal separator driving device 10, the first liquid feed pump 11, the second liquid feed pump 12 and the plurality of passage opening/closing means 81 to 87, a turbidity sensor 14, an optical sensor 15, a weight sensor 16, and plural (in the present embodiment, six) bubble sensors 31, 32, 33, 34, 35 and 36.

Now, first, the circuit for collecting a blood component 2 will be described.

The circuit for collecting a blood component 2 includes the first line (blood collection and blood returning line) 21 that connects the blood collection needle 29 for collecting blood from a donor (blood donor) to the inlet 143 of the centrifugal separator 20, and which has a first pump tube 21g, the second line 22 connected on one end side thereof to the discharge port (outlet) 144 of the centrifugal separator 20, the fourth line (initial flow removing line) (initial flow collection line) 24 connected to a portion of the first line 21 near to the blood collection needle 29, the third line (anticoagulant-injection line) 23, which is connected to the fourth line 24 and has a second pump tube 23a, the tube 50 connected to a portion of the first line 21 on the side of the blood collection needle 29 relative to the pump tube 21g, the tube 49 connected to the tube 50, the tube 43 connected to the second line 22, the tube 44 connected to the tube 43, the plasma collection bag 25 connected to tubes 44 and 49, the tube 42 connected to the second line 22, the air bag 27b connected to the tube 42, the tube 45 connected to the tube 43, the intermediate bag 27a connected to the tube 45, the tube 46 connected to the intermediate bag 27a, the tube 47 connected to the tube 46, the tube 48, the platelet collection bag 26 connected to the tube 48, the tube 51 connected to the platelet collection bag 26, the bag 28 connected to the tube 51, and the initial flow collection bag 61 connected to an end part of the fourth line 24. The air bag 27b and the intermediate bag 27a are formed together as one body (integrated) with each other.

The first line 21 has a blood collection needle side first line 21a to which the blood collection needle 29 is connected, and a centrifugal separator side first line 21b, which is connected on one end side thereof to the blood collection needle side first line 21a and on the other end side thereof to the inlet 143 of the centrifugal separator 20. As the blood collection needle 29, for example, a known metallic needle is used. Incidentally, the blood collection needle 29 constitutes a principal part of the blood collection means.

The blood collection needle side first line 21a, the centrifugal separator side first line 21b, the later-described second line 22, third line 23 and fourth line 24 are each composed of a soft resin-made tube (tube), or a plurality of soft resin-made tubes (tubes) which are connected to each other.

The blood collection needle side first line 21a has a branch connector 21j connected with the fourth line 24, a chamber 21d for removing bubbles and microaggregates, and a branch connector 21f connected with the tube 50, in this order, from the side of the blood collection needle 29.

In addition, bubble sensors 35, 36 and 32, in this order, from the side of the blood collection needle 29 are disposed along the blood collection needle side first line 21a. In this case, the bubble sensors 35 and 36 are disposed between the branch connector 21j and the chamber 21d, while the bubble sensor 32 is disposed between the chamber 21d and the branch connector 21f.

The bubble sensors 35, 36 and 32 are each composed, for example, of a detection means capable of detecting a gas and a liquid (gas/liquid discrimination, gas-liquid interface, or the like) inside the tube by receiving and transmitting ultrasonic waves from the outside of the tube, while utilizing the difference in ultrasonic-wave conductivity between the liquid and the bubbles (gas). The bubble sensors 31, 33 and 34 may also be composed of detection means having the same function as mentioned above.

Incidentally, each of the bubble sensors (gas and liquid detection means) may each be composed of, for example, an optical sensor, an infrared sensor or the like, in place of the above-mentioned ultrasonic sensor.

In addition, a gas-permeable and bacteria-impermeable filter 21i is connected to the chamber 21d through a tube 21h. This line can be used, for example, for detecting the pressure inside of the blood collection needle side first line 21a.

On the other hand, the centrifugal separator side first line 21b is connected to the branch connector 21f that connects with the tube 50, and has a first pump tube 21g formed at an intermediate portion thereof.

The second line 22 is connected on one end side thereof to the discharge port 144 of the centrifugal separator 20. The second line 22 is provided with a branch connector 22b therein for connection to the tubes 42 and 43.

In addition, the turbidity sensor 14 and the bubble sensor 34 are disposed, in this order, from the side of the centrifugal separator 20 along the second line 22. In this case, the turbidity sensor 14 and the bubble sensor 34 are disposed between the centrifugal separator 20 and the branch connector 22b.

Further, a gas-permeable and bacteria-impermeable filter 22f is connected to the branch connector 22b through a tube 41. This line can be used, for example, for detecting the pressure inside of the second line 22.

The fourth line 24 is connected at one end thereof to a branch connector 21j, which is provided in the first line 21. Specifically, the fourth line (passage) 24 branches from the branch connector (first branching portion) 21j, i.e., the fourth line 24 branches from the first line (passage) 21 through the branch connector 21j.

The initial flow collection bag (fourth container) 61 serves as a container for collecting (reserving) the initial flow of the blood (initial blood flow) collected from the donor by the blood collection needle 29. The other end of the fourth line 24 is connected to the initial flow collection bag 61.

The internal volume of the initial flow collection bag 61 is not particularly limited, and is preferably not less than 22.5 mL, and more preferably, is about 30 to 50 mL.

If the internal volume of the initial flow collection bag 61 is less than the aforementioned range, it may be impossible to sufficiently remove (collect) the initial flow of the blood (initial blood flow) collected from the donor by the blood collection needle 29. On the other hand, if the internal volume exceeds this range, the circuit for collecting the blood component 2 becomes large in size.

In addition, one end of a tube 62 is connected to the side of the initial flow collection bag 61, which is opposite to a connection part of the fourth line 24, and a needle pipe 63 is connected to the other end of the tube 62.

An enveloping member 64 for enveloping the needle pipe 63 is disposed along the periphery of the needle pipe 63. Preferably, as the enveloping member 64, for example, a member formed from a film of one of various rubber materials (elastic materials) and which can be easily punctured with the needle tip of the needle pipe 63 may be used.

In addition, a holder 65 having a cap 66 is detachably attached to the base end side of the needle pipe 63, whereby the needle pipe 63 is stored in the holder 65.

The third line 23 is connected at one end thereof to a branch connector 24a, which is provided in the fourth line 24. Specifically, the third line (passage) 23 branches from the branch connector (second branching portion) 24a, i.e., the third line 23 branches from the fourth line (passage) 24 through the branch connector 24a.

Incidentally, the internal volume of the part, existing between the branch connector (first branching portion) 21j and the branch connector (second branching portion) 24a, of the fourth line 24 is not particularly limited, and preferably is about 0.05 to 1 mL, and more preferably, about 0.2 to 0.5 mL. When this configuration is expressed in terms of the length of the part, ranging from the branch connector 21j to the branch connector 24a, of the fourth line 24, the length preferably is about 7 to 140 mm, and more preferably, is about 28 to 70 mm.

This ensures that blood that does not contain any anticoagulant therein, and which stagnates, can securely be prevented from coming into proximity with the first line (blood line) 21, while preventing the circuit for collecting a blood component 2 from increasing in size.

The third line 23 has a second pump tube 23a, a bacteria-removing filter (foreign matter removing filter) 23b, a bubble removing chamber 23c, and an anticoagulant container connecting needle 23d, in this order from the side of the branch connector 24a.

In addition, a bubble sensor 31 is disposed along the third line 23. The bubble sensor 31 is disposed between the branch connector 24a and the second pump tube 23a.

The anticoagulant container connecting needle 23d in the third line 23 is connected to a container (not shown) in which an anticoagulant (anticoagulant solution) is stored (contained). As will be described later, this ensures that the anticoagulant in the container flows in the third line 23 from the anticoagulant container connecting needle 23d toward the branch connector 24a, and then is supplied (injected) into the blood collection needle side first line 21a through a part of the fourth line 24 and the branch connector 21j. This makes it possible to add (mix) the anticoagulant to (into) the blood collected by the blood collection needle 29 through the third line 23, for example.

Incidentally, the anticoagulant is not particularly limited. For example, an ACD-A solution or the like can be used.

In addition, clamps (passage opening/closing means) 91, 92 and 93, which are capable of opening and closing an intermediate portion of the line (passage), are provided respectively in the fourth line 24 between the branch connector 24a and the initial flow collection bag 61, in the blood collection needle side first line 21a between the blood collection needle 29 and the branch connector 21j, and in the blood collection needle side first line 21a on the chamber 21d side of the branch connector 21j in the vicinity of the branch connector 21j. The clamp 91 is provided for opening and closing the passage (passage inside the tube) of the fourth line 24. The clamp 92 is provided for opening and closing the passage (passage inside the tube) of the blood collection needle side first line 21a between the blood collection needle 29 and the branch connector 21j. The clamp 93 is provided for opening and closing the passage (passage inside the tube) of the blood collection needle side first line 21a between the branch connector 21j and the chamber 21d.

The clamp 91 is not reopened after having once been closed during the operation for collecting a blood component. Therefore, a pair of clamps with such a structure, so as not to be opened (difficult to open) after closure thereof, such as a pair of shutter clamps, is preferably used as the clamp 91. In the present embodiment, accordingly, a pair of shutter clamps is used as the clamp 91.

Incidentally, for example, tweezers or the like may be used in place of the clamps 91, 92 and 93.

In a condition in which the clamps 91 and 92 are opened, whereas the clamp 93 is closed, the initial flow of the blood collected from the donor by the blood collection needle 29 flows, due to the donor's venous pressure or head (gravity), from the blood collection needle 29 and through the blood collection needle side first line 21a, the branch connector 21j and the fourth line 24, and ultimately is introduced (collected) into the initial flow collection bag 61. In other words, the initial flow of the blood (initial blood flow) collected from the donor by the blood collection needle 29 is removed from the blood collection needle side first line 21a, through the branch connector 21j and the fourth line 24, and is collected in the initial flow collection bag 61. In this manner, the initial flow of the blood collected, which is likely to be polluted with bacteria, can be easily removed. Accordingly, mixing of the bacteria into each of the blood components (platelets, plasma, etc.) separated from the collected blood is restrained, and safety is enhanced.

Further, in this condition, the liquid feed pump 12 is in a stopped state, so that the initial blood flow is prevented from flowing into the third line 23 through the branch connector 24a. Incidentally, in order to more securely prevent the initial blood flow from flowing into the third line 23 through the branch connector 24a, a pair of clamps may be provided in the third line 23 in the vicinity of the branch connector 24a, such that the clamp is kept closed while the initial blood flow is collected.

In addition, the blood stored in the initial flow collection bag 61 can be collected (sampled) into a vacuum blood collecting tube having a rubber stopper (not shown), for example.

In this case, after the clamp 91 is closed, the cap 66 of the holder 65 is detached, and the vacuum blood collecting tube is inserted into the holder 65 starting from the rubber stopper side thereof. The vacuum blood collection tube then is pushed into the deepest part of the holder 65, and the needle pipe 63 is made to penetrate the rubber stopper. This ensures that the blood stored in the initial flow collection bag 61 flows through the tube 62, whereby the blood is sucked and collected in the vacuum blood collecting tube. After sampling of blood into the vacuum blood collecting tube is completed, the vacuum blood collecting tube is withdrawn from the holder 65. If the blood is sampled into a plurality of vacuum blood collecting tubes, the aforementioned operations are repeated.

The blood collected into the vacuum blood collecting tube can be used, for example, for conducting a biochemical test of serum, an antibody test of infectious viruses (e.g., viruses of AIDS, hepatitis, etc.), or the like.

In addition, a protector 94 is attached to the blood collection needle side first line 21a, between the blood collection needle 21 and the branch connector 21j. The protector 94 can be moved relative to the blood collection needle 21 in the tip end direction (distal direction), from a position that is retracted toward the base end side (proximal side) to a position that covers (stores) the blood collection needle 21. After use, the protector 94 is moved in the tip end direction (distal direction) relative to the blood collection needle 21, so that the blood collection needle 21 is covered with the protector 94.

A plasma collection bag (third container) 25 is a container for collecting (reserving) the plasma (second blood component). One end of the tube 49 is connected to the plasma collection bag 25, and a branch connector 22d is provided at an intermediate part of the tube 49. One end of the tube 50 is connected to the branch connector 22d, whereas the other end thereof is connected to the branch connector 21f.

In addition, one end of the tube 43 is connected to the branch connector 22b, and the branch connector 22c is provided at the other end of the tube 43. One end of the tube 44 is connected to the branch connector 22c, while the plasma collection bag 25 is connected to the other end of the tube 44.

Further, the bubble sensor 33 is disposed along the tube 46 at an intermediate part of the tube 46.

Incidentally, the plasma collection bag 25 and the tubes 43 and 44 constitute a branch line for collecting the plasma and by which the plasma is collected.

The platelet (platelet product) collection bag (second container) 26, which is a blood component collection bag, is a container for collecting (reserving) a platelet containing plasma (first blood component) having passed through a leukocyte removing filter 261 (described later). Incidentally, in the following description, the platelet containing plasma (first blood component) will be referred to as a "platelet concentrate", and the platelet concentrate, which is collected (reserved) in the platelet collection bag 26, will be referred to as a "platelet product".

One end of the tube 51 is connected to the platelet collection bag 26, while the bag 28 is connected to the other end of the tube 51.

The air bag 27b is a container for momentarily storing (reserving) air.

At the time of blood collection, which will be described later, air (sterilized air) in the circuit for collecting a blood component 2, such as in the blood reserving space 146 of the centrifugal separator 20, is transferred into and stored in the air bag 27b. Then, during the blood returning step (blood component returning step), the air stored in the air bag 27b is transferred back into the blood reserving space 146 in the centrifugal separator 20. This ensures that a predetermined blood component, or components thereof, are returned to the donor.

One end of the tube 42 is connected to the branch connector 22b, and the other end is connected to the air bag 27b.

The intermediate bag (momentary reserving bag) (first container) 27a is a container for momentarily reserving the platelet concentrate (first blood component). One end of the tube 45 is connected to the branch connector 22c, and the other end thereof is connected to the intermediate bag 27a.

In addition, one end of the tube 46 is connected to the intermediate bag 27a. A branch connector 22e is provided at the other end of the tube 46. The other end of the tube 49 is connected to the branch connector 22e.

Further, one end of the tube 47 is connected to the branch connector 22e, and a leukocyte removing filter (cell separation filter) 261, for separating and removing leukocytes (predetermined cells) from the platelet concentrate, is disposed at an intermediate part of the tube 47.

In addition, a branch connector 22g is provided at the other end of the tube 47, and a tube 48, which is connected at one end thereof to the platelet collection bag 26, is connected at the other end thereof to the branch connector 22g.

Further, a filter 22h including a filter body, which is provided with a vent filter and a cap therein, is disposed at a port of the branch connector 22g.

The tubes 46 and 47 constitute a supply tube for supplying the platelet concentrate from the intermediate bag 27a to the leukocyte removing filter 261, whereas the tube 48 constitutes a discharge tube, by which the platelet concentrate, having been deprived of leukocytes, is discharged (supplied into the platelet collection bag 26) from the leukocyte removing filter 261.

In other words, the tubes 46, 47 and 48, the intermediate bag 27a, the leukocyte removing filter 261, and the platelet collection bag 26 together constitute a filtration line for separating and removing leukocytes from the platelet concentrate.

In a condition in which the apparatus for collecting a blood component 1 is assembled, the intermediate bag 27a, the leukocyte removing filter 261 and the platelet collection bag 26 are located such that the leukocyte removing filter 261 is positioned below the intermediate bag 27a, and the platelet collection bag 26 is positioned below the leukocyte removing filter 261.

In addition, a filter may be used as the leukocyte removing filter 261, with a configuration in which a filter member composed of a single layer or a stack of two or more layers of a porous material such as a cloth, a nonwoven fabric, a mesh, or a foamed body, etc., of a synthetic resin such as polypropylene, polyester, polyurethane, polyamide, etc., is inserted within a casing provided with an inlet and a discharge port respectively at both ends thereof.

The materials constituting the tubes, the pump tubes 21g, 23a, and the other tubes 41 to 51, 62, 21h used for forming the first to fourth lines 21 to 24, as mentioned above, are preferably polyvinyl chloride.

When the tubes are made of polyvinyl chloride, sufficient pliability and flexibility can be obtained, so that the tubes promise easy handleability and are suited to closing by clamps and the like.

Further, the above-mentioned branch connectors 21f, 21j, 22b, 22c, 22d, 22e, 22g, 24a can be formed from materials that are similar to the aforementioned constituent materials for the tubes.

Incidentally, as the pump tubes 21g and 23a, tubes having strength so as not to be damaged even when pressed by the liquid feed pumps (e.g., roller pumps) 11, 12 (described later) are used.

For each of the plasma collection bag 25, the platelet collection bag 26, the intermediate bag 27a, the air bag 27b, the bag 28, and the initial flow collection bag 61, a bag is used, which is formed by laying resin-made flexible sheet members on each other, while mutually adhering peripheral parts of the sheet members by fusing (heat fusing, microwave fusing, ultrasonic fusing or the like), or by adhesion with an adhesive or the like, in order to form a bag-shaped body. Incidentally, the air bag 27b and the intermediate bag 27a are integrally formed (integrated), as mentioned above.

As the material for forming each of the bags 25, 26, 27a, 27b, 28 and 61, for example, a soft polyvinyl chloride material is used, preferably.

Incidentally, for the sheet member that is used for forming the platelet collection bag 26, even more preferably, a sheet member that is excellent in gas permeability is used, in order to enhance the platelet preservation performance thereof.

Examples of such a sheet member include sheet members made of polyolefins and DnDP plasticized polyvinyl chloride. Alternatively, instead of using such a blank material, a sheet member made of the aforementioned materials, and having a comparatively small thickness (for example, about 0.1 to 0.5 mm, and more particularly, about 0.1 to 0.3 mm), may be used, preferably.

An essential part of the aforementioned circuit for collecting a blood component 2 is configured to be of a cassette type, for example, although this is not shown. Specifically, the circuit for collecting a blood component 2 includes a cassette housing, which partially stores and partially holds the lines (the first line 21, the second line 22 and the third line 23) and the predetermined tubes. In other words, the lines and tubes are partially fixed to the cassette housing.

Both ends of the first pump tube 21g and both ends of the second pump tube 23a are fixed to the cassette housing. The pump tubes 21g and 23a project from the cassette housing in loop shapes corresponding to the shapes of the liquid feed pumps (for example, roller pumps or the like) 11 and 12. Therefore, the first and second pump tubes 21g, 23a are easily attached to the liquid feed pumps 11, 12. In addition, passage opening/closing means 81 to 87 and the like, which will be described later, are disposed within the cassette housing.

The centrifugal separator 20 provided within the circuit for collecting a blood component 2 normally is called a "centrifugal bowl", and operates to separate the blood into a plurality of blood components by means of centrifugal forces.

As shown in FIG. 2, the centrifugal separator 20 includes a pipe body 141, which is provided with a vertically extending inlet 143 at the top end thereof, and a hollow rotor 142 that rotates about the pipe body 141, and which is sealed in a liquid-tight relation to an upper part 145 of the pipe body 141.

The rotor 142 comprises an annular blood reserving space 146 disposed along the peripheral wall inside surface thereof. The blood reserving space 146 has a (tapered) shape, such that the inside and outside diameters thereof gradually decrease along the direction from a lower part toward an upper part in FIG. 2. Also, the lower part communicates with the lower end opening of the pipe body 141 through a substantially circular disk-shaped passage formed along a bottom part of the rotor 142, and the upper part communicates with the discharge port (outlet) 144. Further, in the rotor 142, the volume of the blood reserving space 146 is about 100 to 350 mL, whereas the maximum inside radius (maximum radius) from the axis of rotation of the rotor 142 is about 55 to 65 mm, for example.

The above rotor 142 is rotated under preset predetermined centrifugal conditions (rotating speed and rotating time) by the centrifugal separator driving device 10, which is possessed by the apparatus for collecting a blood component 1. As a result of the centrifugal conditions, a separation pattern (e.g., the number of component parts that are separated) for the blood in the rotor 142 can be set.

As shown in FIG. 2, in the present embodiment, centrifugal conditions are set so that the blood is separated into a plasma layer 131, a buffy coat layer 132, and a red blood cell layer 133, in this order, from the inner layer inside the blood reserving space 146 in the rotor 142.

Next, the entire configuration of the apparatus for collecting a blood component 1, as shown in FIG. 1, shall be described below.

The apparatus for collecting a blood component 1 includes the centrifugal separator driving device 10 for rotating the rotor 142 of the centrifugal separator 20, the first liquid feed pump 11 disposed in an intermediate part of the first line 21, the second liquid feed pump 12 disposed in an intermediate part of the third line 23, a plurality of passage opening/closing means 81, 82, 83, 84, 85, 86 and 87, which are capable of opening and closing an intermediate part of the passage of the circuit for collecting a blood component 2 (the first line 21, the tube 42, the tube 44, the tube 45, the tube 47, the tube 49, and the tube 50), and the controller (control means) 13 for controlling the centrifugal separator driving device 10, the first liquid feed pump 11, the second liquid feed pump 12, and the plurality of passage opening/closing means 81 to 87.

Moreover, the apparatus for collecting a blood component 1 further includes the turbidity sensor 14 mounted (disposed) in the second line 22, the optical sensor 15 disposed in the vicinity of the centrifugal separator 20, the plural bubble sensors 31 to 36, and the weight sensor 16 for measuring the weight of the plasma on the basis of each plasma collection bag 25.

The controller 13 comprises two pump controllers (not shown) for the first liquid feed pump 11 and the second liquid feed pump 12, respectively. The controller 13 and the first and second liquid feed pumps 11, 12 are electrically connected through the pump controllers.

A driving controller (not shown) included within the centrifugal separator driving device 10 is electrically connected to the controller 13.

The passage opening/closing means 81 to 87 each are connected electrically to the controller 13.

In addition, the turbidity sensor 14, the optical sensor 15, the weight sensor 16, and the bubble sensors 31 to 36 each are connected electrically to the controller 13.

The controller 13 is composed, for example, from a microcomputer, wherein detection signals from the turbidity sensor 14, the optical sensor 15, the weight sensor 16, and the bubble sensors 31 to 36 are each input on occasion to the controller 13.

Based on the detection signals from the turbidity sensor 14, the optical sensor 15, the weight sensor 16 and the bubble sensors 31 to 36, and according to a preset program, the controller 13 controls operations of each part of the apparatus for collecting a blood component 1. Specifically, the controller 13 controls the rotation, the stop and rotating direction (normal rotation/reverse rotation) of each of the liquid feed pumps 11, 12 and, if necessary, the opening/closing of the passage opening/closing means 81 to 87 along with operation of the centrifugal separator driving device 10.

The first passage opening/closing means 81 is provided for opening and closing the passage of the first line 21 on the blood collection needle 29 side relative to the first pump tube 21g, i.e., between the branch connector 21f and the chamber 21d.

The second passage opening/closing means 82 is provided for opening and closing the passage in the tube 50. The third passage opening/closing means 83 is provided for opening and closing the passage in the tube 44. The fourth passage opening/closing means 84 is provided for opening and closing the passage in the tube 45. The fifth passage opening/closing means 85 is provided for opening and closing the passage in the tube 42. The sixth passage opening/closing means 86 is provided for opening and closing the passage in the tube 49. The seventh passage opening/closing means 87 is provided for opening and closing the passage in the tube 47.

The passage opening/closing means 81 to 87 have insertion parts, into which the first line 21 and the tubes 50, 44, 45, 42, 49, 47 can be inserted, respectively. Clamps, which are operated by a drive source such as a solenoid, an electric motor, or a cylinder (oil hydraulic or pneumatic), are provided at the insertion parts. Preferably, electromagnetic clamps operated by solenoids are provided.

The passage opening/closing means (clamps) 81 to 87 are operated respectively based on signals from the controller 13.

The centrifugal separator driving device 10, as shown in FIG. 2, includes a housing 201 for storing the centrifugal separator 20, a base part 202, a motor 203 serving as a drive source, and a circular disk-shaped fixing base 205 for holding the centrifugal separator 20.

The housing 201 is mounted on and fixed to an upper portion of the base part 202. In addition, the motor 203 is fixed by bolts 206 to a lower surface of the housing 201 through a spacer 207.

The fixing base 205 is fitted over a tip part of the rotating shaft 204 of the motor 203, so as to be rotated coaxially and integrally with the rotating shaft 204. Also, the fixing base 205 is provided with a recess on an upper part thereof, into which a bottom part of the rotor 142 is fitted.

In addition, the upper part 145 of the centrifugal separator 20 is fixed to the housing 201 through a fixing member (not shown).

In the above-described centrifugal separator driving device 10, when the motor 203 is driven, the fixing base 205 and the rotor 142 fixed thereto are rotated at a rotating speed of about 3000 to 6000 rpm, for example.

The optical sensor 15 is disposed at a side portion (on the left side in FIG. 2) of the housing 201.

The optical sensor 15 is configured so as to cast light toward the blood reserving space 146 and to receive reflected light therefrom.

The optical sensor 15 radiates (casts) light (e.g., a laser beam) from a light casting part 151, and receives the reflected light reflected by a reflective surface 147 of the rotor 142 at a light receiving part 152. At the light receiving part 152, the received light is converted into electrical signals according to the quantity of light received.

The optical sensor 15 includes a reflector 153 having a reflective surface on one side thereof, and operates to change the optical path. The optical sensor is configured such that light radiated from the light casting part 151 is radiated onto the reflective surface 147 through the reflector 153. Also, light reflected by the reflective surface 147 is received by the light receiving part 152 through the reflector 153.

In this instance, the cast light and the reflected light are each transmitted through the blood components in the blood reserving space 146. In this case, the presence ratio between the blood components at the position where the cast light and the reflected light are transmitted differs depending on the position of the interface between the blood components (in this embodiment, the interface B between the plasma layer 131 and the buffy coat layer 132), so that the transmittance thereof varies. As a result, the quantity of light received at the light receiving part 152 fluctuates (varies), and the fluctuation can be detected as a variation in the output voltage from the light receiving part 152.

Specifically, the optical sensor 15 can detect the position of the interface between the blood components, based on a variation in the quantity of light received at the light receiving part 152.

Incidentally, the interface between the blood components, which is detected by the optical sensor 15, is not limited to the interface B. For example, the interface to be detected may be an interface between the buffy coat layer 132 and the red blood cell layer 133.

Layers 131 to 133 in the blood reserving space 146 have different colors according to the blood components. Especially, the red blood cell layer 133 has a red color in accordance with the color of the red blood cells. Therefore, there exists a preferable range as to the wavelength of the cast light, from the viewpoint of enhancing the accuracy of the optical sensor 15. The wavelength range is not particularly limited. For example, the wavelength range is preferably about 600 to 900 nm, and more preferably, about 750 to 800 nm.

The turbidity sensor 14 detects a turbidity of the fluid flowing in the second line 22, and outputs a voltage value according to such turbidity. Specifically, a low voltage value is output when turbidity is high, and a high voltage value is output when turbidity is low.

The turbidity sensor 14 can detect, for example, a variation in the concentration of platelets in the plasma flowing in the second line 22, along with mixing of red blood cells into the plasma, or the like.

In addition, by the bubble sensor 34, it is possible to detect, for example, a replacement from air to plasma in the fluid flowing through the second line 22.

An ultrasonic sensor, an optical sensor, an infrared sensor or the like can be used as the turbidity sensor 14 and the bubble sensors 31 to 36.

Concerning the first liquid feed pump 11, to which the first pump tube 21g is attached, and the second liquid feed pump 12, to which the second pump tube 23a is attached, a non-blood-contacting type pump, such as a roller pump, preferably is used.

Further, a pump capable of feeding blood in either of both directions is used as the first liquid feed pump (blood pump) 11. Specifically, a roller pump is used, which is capable of both normal rotation and reverse rotation.

The apparatus for collecting a blood component 1 includes a supply means for supplying an anticoagulant into the passage of the fourth line 24 (for adding an anticoagulant to the blood). The supply means is configured so as to supply the anticoagulant, into the first line 21 through the third line (anticoagulant-injection line) 23, the branch connector 24a, a portion of the fourth line 24, and the branch connector 21j, after a predetermined amount of initial blood flow is removed (collected) through the fourth line 24. Concerning the function (means) for supplying the anticoagulant into the first line 21, an essential part thereof comprises the second liquid feed pump 12 and the controller 13, wherein the supplying liquid feed pump is composed of the second liquid feed pump 12.

This makes it possible to prevent blood that does not contain any anticoagulant from stagnating in the fourth line 24 between the branch connector 21j and the branch connector 24a, as well as in the branch connector 21j, which could result in coagulation of the stagnating blood.

Next, actions (operations) of the apparatus for collecting a blood component 1 shall be described below.

First, a platelet collection process (blood component collection process) conducted using the apparatus for collecting a blood component 1 will be described.

The apparatus for collecting a blood component 1 operates to carry out a platelet collection process (blood component collection process), including a first plasma collection step, a constant-speed plasma circulation step, a second plasma collection step, an accelerated plasma circulation step, a third plasma collection step, a platelet collection step, and a blood returning step (blood component returning step), under the control of the controller 13.

The first plasma collection step, the constant-speed plasma circulation step, the second plasma collection step, the accelerated plasma circulation step, the third plasma collection step, and the platelet collection step constitute the blood component collection step. By carrying out the blood component collection step, plasma is collected in the plasma collection bag 25, whereas the platelet concentrate is collected in the intermediate bag 27a. In addition, by carrying out the blood returning step, blood components (residual blood components) (mainly, red blood cells and leukocytes) remaining in the blood reserving space 146 in the rotor 142 of the centrifugal separator 20 are discharged from the inlet 143 of the centrifugal separator 20, and are returned to the donor through the first line 21 (the blood collection needle 29). In component-basis blood collection, the platelet collection process, including the blood component collection step and the blood returning step, is conducted at least one time (one cycle). Incidentally, the platelet collection process usually is conducted a plurality of times (in a plurality of cycles).

The platelet collection process may also be conducted, for example, by the method described in Japanese Laid-Open Patent Publication No. 2005-110748 or the like, although there is some difference in the circuit configuration.

Further, concurrently with the final cycle of the platelet collection process, or after completion of the final cycle of the platelet collection process, the apparatus for collecting a blood component 1 performs a filtration process (filtration step), in which the platelet concentrate momentarily collected (reserved) in the intermediate bag 27a is supplied to the leukocyte removing filter 261 in order to filter the platelet concentrate (i.e., separate and remove white corpuscles present in the platelet concentrate) under the control of the controller 13.

During the filtration process, the seventh passage opening/closing means 87 is opened. This ensures that the platelet concentrate in the intermediate bag 27a is transferred, through the tubes 46, 47, the leukocyte removing filter 261 and the tube 48, into the platelet collection bag 26 under the head (gravity). In this case, most of the platelet concentrate is permitted to pass through the filter member of the leukocyte removing filter 261, whereas the leukocytes are trapped by the filter member. Therefore, leukocytes in the platelet product can be removed at a very high removal ratio.

Incidentally, transfer of the platelet concentrate from the intermediate bag 27a into the platelet collection bag 26 may be carried out using a pump.

In addition, prior to the first cycle of the platelet collection process, a priming process (priming step) and a process (step) for removing (collecting) the initial blood flow are conducted, in this order.

Next, the steps ranging from the priming step to the step of removing the anticoagulant and the initial blood flow (the step prior to the first cycle of the platelet collection process) shall be described below.

[1] First, the clamp 93 is opened, whereas clamps 91 and 92 are closed. In this condition, the third line 23, a part of the fourth line 24 that ranges between the branch connector 24a and the branch connector 21j, and a part of the first line 21 that ranges from the branch connector 21j of the blood collection needle side first line 21a to the bubble sensor 35 (or 36), are primed with an anticoagulant.

Specifically, the second liquid feed pump 12 is operated under control of the controller 13. This ensures that the anticoagulant flows from the third line 23, through the branch connector 24a and the fourth line 24 toward the first line 21, and then flows through the branch connector 21j in the first line 21 toward the bubble sensor 35. As a result, the third line 23, a portion of the fourth line 24 that ranges between the branch connector 24a and the branch connector 21j, and a portion of the first line 21 that ranges from the branch connector 21j of the blood collection needle side first line 21a to the bubble sensor 35 (or 36), are primed with the anticoagulant. Priming is completed when the anticoagulant is detected by the bubble sensors 31 and 35 (or 36), and the second liquid feed pump 12 is stopped. In addition, the clamp 93 is closed.

The priming step may be conducted such that only the third line 23 is primed. Specifically, transfer of the anticoagulant may be finished after being conducted for the portion of the third line 23, which ranges between the bubble sensor 31 and the branch connector 24a. In this case, when the initial blood flow is collected in the subsequent step [2], contact between the initial blood flow in the fourth line 24 and the anticoagulant in the third line 23 is inhibited by an air layer (air). Thus, the anticoagulant can be prevented from mixing into the initial blood flow, whereby the initial blood flow reserved in the initial flow collection bag 61 can be used as blood for testing purposes.

[2] Next, centesis of a blood vessel of the donor (blood donor) is conducted through the blood collection needle 29 while the clamps 91 and 92 are opened. The clamp 93 is kept closed.

As a result, the initial flow of blood (initial blood flow) collected from the donor by the blood collection needle 29 flows, due to the donor's venous pressure or head (gravity), through the blood collection needle 29, the blood collection needle side first line 21a, the branch connector 21j, and the fourth line 24, such that the blood is introduced into (collected in) the initial flow collection bag 61.

When a predetermined amount of blood has been collected in the initial flow collection bag 61, the clamp 91 is closed, and collection of the initial blood flow is finished.

Incidentally, step [2], as well as the aforementioned step [1], are conducted only before the first cycle of the platelet collection process.

When step [2] is finished, the clamp 93 is opened, and a subsequent step (the first cycle of the platelet collection process) is initiated. Descriptions of the subsequent steps have been omitted.

As has been described above, according to the present apparatus for collecting a blood component 1, the presence of the fourth line 24 ensures that the initial flow of the collected blood (initial blood flow), which is highly likely to be polluted with bacteria, can be easily removed at the time of blood collection. Therefore, mixing of the bacteria into the collected platelet concentrate, platelet product or plasma is restrained, and safety is enhanced.

In addition, the initial blood flow, removed as described above, can be reserved in the initial flow collection bag 61.

Further, after a predetermined amount of the initial blood flow is removed (collected), the anticoagulant is supplied into the first line 21 through the third line 23, the branch connector 24a and the branch connector 21j. Therefore, it is possible to prevent blood that does not contain any anticoagulant from stagnating in the fourth line 24, between the branch connector 24a and the branch connector 21j, as well as in the branch connector 21j, which could result in coagulation of the stagnating blood. If blood were to become coagulated in the branch connector 21j, the coagulated blood might flow (circulate) in the circuit or become mixed in the plasma collection bag 25 or in the intermediate bag 27a during blood collection, and could be returned to the donor when the blood is returned, or could potentially plug up the passage. On the other hand, in the present apparatus for collecting a blood component 1, such a situation can be prevented assuredly, and component-basis blood collection can be carried out safely and securely, without increasing the burden on the donor.

In addition, since component-basis blood collection can be securely carried out, the advantage of component-basis blood collection is prevented from being spoiled, in that the interval of blood collection is short as compared with whole blood collection.

Further, in the present apparatus for collecting a blood component 1, leukocytes are separated and removed from the platelet concentrate (which are separated and collected from the blood) by the leukocyte removing filter 261, so that a platelet product can be obtained with an extremely low possibility of having leukocytes mixed therein.

While the circuit for collecting a blood component and the apparatus for collecting a blood component according to the present invention have been described above based on an embodiment thereof shown in the drawings, the invention is not limited to the above embodiment. The configurations of each part may be replaced with any arbitrary configuration having the same or equivalent function. Moreover, other arbitrary structures or steps may be added to the present invention.

Incidentally, the present invention is not limited to being applied to a case of obtaining a platelet product and a plasma product (or a raw material plasma for a plasma fractional product). The invention may be applied, for example, to a case in which only one of a platelet product and a plasma product is obtained from the blood. Specifically, in the present invention, the blood component collected in the blood component collection bag may be either one of platelets (platelets including the plasma) and the plasma.

In addition, the present invention is not limited to being applied to cases of obtaining a platelet product and/or a plasma product. The invention may be applied, for example, to cases in which a red blood cell product, a leukocyte product and/or the like are obtained from the blood. Specifically, in the present invention, the blood component collected in the blood component collection bag is not limited to platelets (platelets including the plasma) and plasma, but may also include red blood cells (red blood cells containing plasma), leukocyte products (leukocytes containing plasma), or the like.

Further, in the present invention, the cells that are separated and removed by the cell separating filter are not limited to leukocytes.

In addition, in the present invention, the optical sensor is not limited to the optical sensor illustrated in the drawings. The optical sensor may comprise, for example, a line sensor or the like.

Further, in the present invention, the blood separator is not limited to being a centrifugal-type of separator, and may, for example, comprise a membrane-type blood separator or the like.

In addition, the system of the apparatus for collecting a blood component according to the present invention is not limited to an intermittent-type of system, and may, for example, also comprise a continuous-type of system.

Industrial Applicability

The circuit for collecting a blood component according to the present invention includes a blood collection means provided with a blood collection needle for collecting blood from a blood donor, a blood separator for separating the blood collected by the blood collection means, a blood component collection bag for collecting a predetermined blood component separated by the blood separator, a blood line connecting the blood collection needle and the inlet of the blood separator, an initial flow removing line branching from a first branching portion formed in the blood line for removing an initial flow of blood collected from the blood donor, and an anticoagulant-injection line branching from a second branching portion formed in the initial flow removing line for injecting an anticoagulant. Therefore, the initial flow of blood that is collected (initial blood flow), which is likely to be polluted with bacteria, can easily be removed at the time of blood collection. Thus, mixing of bacteria into the collected blood or the blood component(s) separated from the collected blood can be restrained, thereby enhancing safety. In addition, after a predetermined amount of initial blood flow is removed, the anticoagulant is supplied into the blood line (blood collection line) through the initial flow removing line. Therefore, it is possible to prevent blood that does not contain any anticoagulant from stagnating at the branch point of the initial flow removing line within the blood line, with the result of coagulation of the stagnating blood. If blood is coagulated in the branch connector, the coagulated blood might flow (circulate) in the circuit or mix into the plasma collection bag during blood collection. Additionally, the coagulated blood could be returned to the donor (blood donor) when the blood is returned, or the coagulated blood might plug up the passage. On the other hand, in the present invention, such a situation can be prevented assuredly, and component-basis blood collection can be carried out safely and assuredly, without increasing the burden on the donor. Therefore, the circuit for collecting a blood component according to the present invention has industrial applicability.

The invention claimed is:

1. An apparatus for collecting a blood component, wherein said apparatus separates a blood collected from a blood donor to collect the predetermined blood component, comprising:
   a circuit for collecting a blood component comprising:
      a blood collection needle for collecting blood from a blood donor;
      a blood separator for separating said blood collected by said blood collection needle:
      a blood component collection bag for collecting a predetermined blood component separated by said blood separator:
      a blood line connecting said blood collection needle and the inlet of said blood separator;
      an initial flow removing line branched from a first branching portion formed in said blood line for removing initial flow of said blood collected from the blood donor; and
      an anticoagulant-injection line branched from a second branching portion formed in said initial flow removing line for injecting an anticoagulant,
      wherein an internal volume of a portion, between said first branching portion and said second branching portion of said initial flow removing line is 0.05 to 1 mL; and
   a supply means for adding said anticoagulant to said blood collected by said blood collection needle,
   wherein said supply means comprises a priming mechanism including a pump for feeding anticoagulant through the anticoagulant-injection line, and a sensor which detects the presence of anticoagulant in the anticoagulant-injection line at a location spaced from the second branching portion and, in response to such detection, shuts off the pump to prevent the anticoagulant from reaching the second branching portion;
   wherein a subsequently performed collection of the initial flow of blood occurs with the initial flow of blood being separated from the anticoagulant by air in the anticoagulant-injection line, so the initial flow of blood can be collected in a state free of anticoagulant.

2. The apparatus for collecting a blood component according to claim 1, wherein said supply means comprises a liquid feed pump disposed within said anticoagulant-injection line.

3. The apparatus for collecting a blood component according to claim 1, wherein said apparatus for collecting a blood component performs at least one cycle of a blood component collection process, including a blood component collection step by which the collected blood is separated and said predetermined blood component is collected therefrom, and a blood component returning step in which residual blood components are returned.

4. The apparatus for collecting a blood component according to claim 1, wherein said apparatus for collecting a blood component performs at least one cycle of a platelet collection process including:
   a plasma collection step in which the collected blood is separated and plasma is collected;
   a plasma circulation step in which said plasma collected by said plasma collection step is circulated in said blood separator;
   a platelet collection step in which said plasma collected by said plasma collection step is accelerated and supplied into said blood separator, whereby platelets are collected; and
   a blood component returning step in which residual blood components are returned.

5. The apparatus for collecting a blood component according to claim 1, wherein the circuit for collecting a blood component further comprises an initial flow collecting bag connected to said initial flow removing line to retain the initial flow of said blood.

6. The apparatus for collecting a blood component according to claim 5, wherein the circuit for collecting a blood component further comprises:

a first clamp provided in said initial flow removing line between said second branching portion and said initial flow collecting bag;

a second clamp provided in said blood line between said blood collection needle and said first branching portion; and a third clamp provided in said blood line between said first branching portion and said blood separator.

7. The apparatus for collecting a blood component according to claim 1, further including an initial flow collection bag communicating with the initial flow removing line for collecting the initial flow of blood.

8. The apparatus for collecting a blood component according to claim 1, wherein said supply means supplies said anticoagulant to said blood line through said anticoagulant-injection line, said second branching portion, a part of said initial flow removing line, and said first branching portion, after said initial flow of said blood is removed through said initial flow removing line.

9. An apparatus for collecting a blood component, wherein the apparatus separates a blood collected from a blood donor to collect the predetermined blood component, comprising:

a circuit for collecting a blood component comprising:
  a blood collection needle for collecting blood from a blood donor;
  a blood separator for separating the blood collected by the blood collection needle:
  a blood component collection bag for collecting a predetermined blood component separated by the blood separator:
  a blood line connecting the blood collection needle and the inlet of the blood separator;
  an initial flow removing line branched from a first branching portion formed in the blood line for removing initial flow of the blood collected from the blood donor; and
  an anticoagulant-injection line branched from a second branching portion formed in the initial flow removing line for injecting an anticoagulant,
  wherein a length of the initial flow removing line between the first branching portion and the second branching portion of 7 mm to 140 mm so that blood which does not contain any anticoagulant and which stagnates is prevented from coming into proximity with the blood line; and a supply means for adding the anticoagulant to the blood collected by the blood collection needle, wherein the supply means comprises a priming mechanism including a pump for feeding anticoagulant through the anticoagulant-injection line, and a sensor which detects the presence of anticoagulant in the anticoagulant-injection line at a location spaced from the second branching portion and, in response to such detection, shuts off the pump to prevent the anticoagulant from reaching the second branching portion;

wherein a subsequently performed collection of the initial flow of blood occurs with the initial flow of blood being separated from the anticoagulant by air in the anticoagulant-injection line, so the initial flow of blood can be collected in a state free of anticoagulant.

10. The apparatus for collecting a blood component according to claim 9, wherein said supply means comprises a liquid feed pump disposed within said anticoagulant-injection line.

11. The apparatus for collecting a blood component according to claim 9, wherein said apparatus for collecting a blood component performs at least one cycle of a blood component collection process, including a blood component collection step by which the collected blood is separated and said predetermined blood component is collected therefrom, and a blood component returning step in which residual blood components are returned.

12. The apparatus for collecting a blood component according to claim 9, wherein said apparatus for collecting a blood component performs at least one cycle of a platelet collection process including:

a plasma collection step in which the collected blood is separated and plasma is collected;

a plasma circulation step in which said plasma collected by said plasma collection step is circulated in said blood separator;

a platelet collection step in which said plasma collected by said plasma collection step is accelerated and supplied into said blood separator, whereby platelets are collected; and a blood component returning step in which residual blood components are returned.

13. The apparatus for collecting a blood component according to claim 9, wherein the circuit for collecting a blood component further comprises an initial flow collecting bag connected to said initial flow removing line to retain the initial flow of said blood.

14. The apparatus for collecting a blood component according to claim 13, wherein the circuit for collecting a blood component further comprises:

a first clamp provided in said initial flow removing line between said second branching portion and said initial flow collecting bag;

a second clamp provided in said blood line between said blood collection needle and said first branching portion; and a third clamp provided in said blood line between said first branching portion and said blood separator.

15. The apparatus for collecting a blood component according to claim 9, further including an initial flow collection bag communicating with the initial flow removing line for collecting the initial flow of blood.

16. The apparatus for collecting a blood component according to claim 9, wherein said supply means supplies said anticoagulant to said blood line through said anticoagulant-injection line, said second branching portion, a part of said initial flow removing line, and said first branching portion, after said initial flow of said blood is removed through said initial flow removing line.

* * * * *